(12) United States Patent
Mailhe et al.

(10) Patent No.: US 12,102,423 B2
(45) Date of Patent: Oct. 1, 2024

(54) AUTONOMOUS MAGNETIC RESONANCE SCANNING FOR A GIVEN MEDICAL TEST

(71) Applicant: Siemens Healthineers AG, Forchheim (DE)

(72) Inventors: Boris Mailhe, Plainsboro, NJ (US); Dorin Comaniciu, Princeton, NJ (US); Ali Kamen, Skillman, NJ (US); Mariappan S. Nadar, Plainsboro, NJ (US); Bin Lou, Princeton Junction, NJ (US); Andreas Greiser, Erlangen (DE); Venkata Veerendranadh Chebrolu, Rochester, MN (US)

(73) Assignee: Siemens Healthineers AG, Forchheim (DE)

( * ) Notice: Subject to any disclaimer, the term of this patent is extended or adjusted under 35 U.S.C. 154(b) by 225 days.

(21) Appl. No.: 17/807,218

(22) Filed: Jun. 16, 2022

(65) Prior Publication Data

US 2023/0248255 A1    Aug. 10, 2023

Related U.S. Application Data

(60) Provisional application No. 63/308,508, filed on Feb. 10, 2022.

(51) Int. Cl.
*A61B 5/05*    (2021.01)
*A61B 5/00*    (2006.01)
(Continued)

(52) U.S. Cl.
CPC ............ *A61B 5/055* (2013.01); *A61B 5/0077* (2013.01); *A61B 5/704* (2013.01); *A61B 5/7221* (2013.01); *A61B 5/7264* (2013.01); *G01R 33/543* (2013.01)

(58) Field of Classification Search
CPC ....... A61B 5/055; A61B 5/0077; A61B 5/704; A61B 5/7221; A61B 5/7264
See application file for complete search history.

(56) References Cited

U.S. PATENT DOCUMENTS 10,783,655 B2    9/2020  Zhao et al.
2011/0210734 A1   9/2011  Darrow et al.
(Continued)

OTHER PUBLICATIONS

European Search Report for Corresponding EP Application No. EP23156034.3, dated Aug. 10, 2023.
(Continued)

*Primary Examiner* — Joel F Brutus (57) ABSTRACT

For autonomous MR scanning for a given medical test, a simplified MR scanner may be used without or will little input or control by a technologist (e.g., by a physician, radiologist, or person trained in MR scanner operation). The MR scanner autonomously positions, scans, checks quality, analyzes, and/or outputs an answer to a diagnostic question with or without an MR image. Scan analysis, based on artificial intelligence, allows for on-going or on-the-fly alteration of the scanning configuration to acquire the data desired to answer the diagnostic question. By using a simplified MR scanner, both position of the patient relative to the MR scanner and localization of the scan by the MR scanner are jointly solved. Sensors may sense a patient in a scan position where the reduced radio frequency requirements allow for a more open bore.

19 Claims, 4 Drawing Sheets (51) Int. Cl.
*A61B 5/055* (2006.01)
*G01R 33/54* (2006.01)

(56) References Cited

U.S. PATENT DOCUMENTS

| | | |
|---|---|---|
| 2011/0228998 A1 | 9/2011 | Vaidya et al. |
| 2018/0228460 A1 | 8/2018 | Singh et al. |
| 2020/0088824 A1 | 3/2020 | Takeshima |
| 2020/0134887 A1 | 4/2020 | Zeng et al. |
| 2021/0364589 A1* | 11/2021 | Bilgic .................. A61B 5/7207 |
| 2021/0391064 A1* | 12/2021 | Sisodia ................ G01C 21/206 |

OTHER PUBLICATIONS

Wang, Jian, et al. "A review of deep learning on medical image analysis." Mobile Networks and Applications 26 (2021): 351-380.
David Y. Zeng, et al. "Reinforcement Learning for Online Sampling Optimization for Magnetic Resonance Imaging" 32nd Conference on Neural Information Processing Systems (NIPS 2018), Montreal, Canada. pp. 1-4.
Loktyushin, Alexander, et al. "MRzero-Automated discovery of MRI sequences using supervised learning." Magnetic Resonance in Medicine 86.2 (2021): 709-724.
Partial European Search Report for Corresponding EP Application No. EP23156024, received Jun. 26, 2003.

* cited by examiner

AUTONOMOUS MAGNETIC RESONANCE SCANNING FOR A GIVEN MEDICAL TEST

RELATED APPLICATIONS

The present patent document claims the benefit of the filing date under 35 U.S.C. § 119(e) of Provisional U.S. Patent Application Ser. No. 63/308,508, filed Feb. 10, 2022, which is hereby incorporated by reference.

BACKGROUND

Magnetic resonance (MR) imaging devices are currently built to fit a manual workflow where the scanner first reconstructs images, and then those images are shown to a radiologist for reading. This comes with multiple shortcomings. First, since reconstruction is a deterministic function of the acquired data, reconstruction suppresses information. While some of that suppression may be beneficial (e.g., in presence of noise), the criteria to decide what to keep and what to suppress are subjective and only loosely linked to the clinical decision being answered. Second, a lot of the current MR imaging inner workings are designed to simplify the reconstruction task rather than to optimize the information rate of the scan. Finally, those simplifying assumptions also put high requirements on the MR hardware. K-space sampling for reconstruction requires linear gradients, and spatially constant image contrast requires homogeneous B0 and B1 fields. These hardware requirements result in more costly MR imaging devices.

SUMMARY

By way of introduction, the preferred embodiments described below include methods, systems, instructions, and non-transitory computer readable media for autonomous MR scanning for a given medical test. A simplified MR scanner may be used without or will little input or control by a technologist (e.g., by a physician, radiologist, or person trained in MR scanner operation). The MR scanner autonomously positions, scans, checks quality, analyzes, and/or outputs an answer to a diagnostic question with or without an MR image. Scan analysis, based on artificial intelligence, allows for on-going or on-the-fly alteration of the scanning configuration to acquire the data desired to answer the diagnostic question. By using a simplified MR scanner, both position of the patient relative to the MR scanner and localization of the scan by the MR scanner are jointly solved. Sensors may sense a patient in a scan position where the reduced radio frequency requirements allow for a more open bore.

In a first aspect, a method of data analytics is provided for magnetic resonance (MR) scanning. An MR scanner scans a patient using a first configuration based on a medical test during a MR examination, resulting in first raw data. A first machine-learned model analyzes the first raw data, resulting in a change of the first configuration. A second configuration based on the change from the first configuration controls the MR scanner. The MR scanner scans the patient using the second configuration for the medical test as part of the same MR examination, resulting in second raw data. A diagnostic output of the medical test of the MR examination is output from the first and second raw data.

In one embodiment, the MR scanning is with a non-uniform main magnetic field, non-homogeneous first pulses, and/or non-linear gradients.

In another embodiment, the analyzing includes determining a value for a diagnosis for the medical test by the first machine-learned model and an uncertainty for the value. The controlling includes altering from the first configuration to the second configuration where the uncertainty is above a threshold. For example, next measurements are proscribed based on back-propagation of the first machine-learned model. Parameters of the second configuration are set for the next measurements based on missing information identified by the backpropagation.

As another embodiment, analyzing includes determining that insufficient information has been gathered by the MR scanning using the first configuration, and controlling includes determining the second configuration to gain the information.

In yet another embodiment, analyzing includes inputting the first raw data and the first configuration to the first machine-learned model and outputting by the first machine-learned model the diagnostic output as an answer to a diagnostic question.

Further embodiments include: positioning a patient relative to the MR scanner and localizing the MR scanning by a second machine-learned model solving for both the positioning and the localizing; and checking quality of the first raw data by a second machine-learned model, wherein controlling includes controlling to increase the quality without input from a human.

As yet another embodiment, controlling includes controlling by a second machine-learned model, the second machine-learned model being a reinforcement learned model. In some embodiments, the MR scanning using the first configuration continues until the reinforcement learned model generates the change.

In a second aspect, a magnetic resonance (MR) system includes a MR scanner configured by settings of controls to scan a region of a patient. The scan provides scan data. A patient support for the patient is moveable relative to the MR scanner. A sensor is configured to sense the patient on the patient support. A processor is configured to jointly (1) position the patient by movement of the patient support and/or the MR scanner and (2) localize the scan of the region by the MR scanner.

In one embodiment, the processor includes a machine-learned detector configured to detect the position and localization from input of an output of the sensor and the scan data and includes a machine-learned actor configured to move the patient support and change the localization when the detected position and localization is incorrect.

As another embodiment, the processor includes a machine-learned model configured to jointly position and localize as a single solution for both the position and the localization.

In other embodiments, the processor is further configured to analyze the scan data once the patient is positioned and the scan localized. The analysis is by a machine-learned model configured to output a diagnosis in response to input of the scan data. The processor is further configured to alter the settings based on the analysis.

In another embodiment, the processor is further configured to monitor artifacts of the scan data and alter the settings based on artifact level.

In yet another embodiment, the sensor is a camera, and the MR scanner is an open bore MR scanner where a field of view of the camera extends to the patient while localized within an open bore of the open bore MR scanner.

In a third aspect, a method is provided for autonomous magnetic resonance (MR) scanning. a patient is positioned in an MR scanner. A region of the patient is localized by the MR scanner for scanning the region. The MR scanner scans the patient, resulting in scan data. The scan data is analyzed, and a diagnostic answer is generated from the scan data. The positioning, localizing, MR scanning, analyzing, and generating are performed without human control.

According to one embodiment, analyzing includes checking quality of the scan data by a machine-learned model. A processor alters a configuration of the MR scanner based on the quality. In one example, checking includes checking by the machine-learned model as a machine-learned generator of quality used to identify deviation from the quality regardless of a type of artifact. In another example, checking includes checking for a type of artifact, where altering includes altering the configuration to reduce the type of artifact.

The present invention is defined by the following claims, and nothing in this section should be taken as a limitation on those claims. Further aspects and advantages of the invention are discussed below in conjunction with the preferred embodiments and may be later claimed independently or in combination.

DETAILED DESCRIPTION

The data acquired by an MR scanner is leveraged by enabling end-to-end data artificial intelligence (AI) analytics from raw signals to clinical findings. This end-to-end approach both improves and standardizes performance. Being able to directly analyze the acquired data allows relaxation of hardware requirements and/or may enable shorter protocols. Relaxing hardware constraints reduces costs by reduction in design requirements, allowing more accessible MR devices. Devices with relaxed design may not provide images or useful images but may provide analytics as a way to understand the captured measurements. The image reconstruction step may be skipped. Fully automated, low-cost MR devices may be provided where image reconstruction is not the goal. The MR devices are not built to produce images in the first place. Focusing on scanning for data analytics may also enable faster protocols on high-field (i.e., image quality) scanners in autonomous operation.

In autonomous MR scanning, the scanning may adapt during a given examination of a patient. Rather than follow a scanning protocol for imaging, controls of the MR device are adapted to perform a given medical test. The scanning protocol adapts so that a test can be performed with minimal supervision from a technologist. AI analyzes the acquired data and reconfigures the MR scanner to acquire data most useful for answering the diagnostic question.

AI may be used to control patient positioning and region of interest (ROI) localization to further aid autonomous scanning. The positioning and localization may be jointly solved rather than sequentially, such as where a sensor other than MR may sense the patient even when within the MR scanner.

AI may be used for quality monitoring during the scan to further aid autonomous scanning. The continuous quality monitoring occurs during the scan, allowing analysis to control the scan without human input during the examination.

In one embodiment, MR is automated for a simplified MR scanner, reducing the technical burden placed on the operator and enabling widespread deployments in settings without access to a skilled technologist. Automation provides self-service workflows in which the patient performs their own scan under guidance from the device. This automation is performed using the protocol optimization of the scanning with the aim of reducing development costs of the MR scanner. By using AI configuration based on data analysis during the scan, a more simplified MR scanner may be used. This can be especially important for low-cost hardware that breaks standard MR assumptions and the resulting sequence development heuristics. Real-time control allows the scanner to adapt online to the data already acquired. This can potentially result in more efficient tailored protocols than a one-size-fits-all approach.

Figure 1:
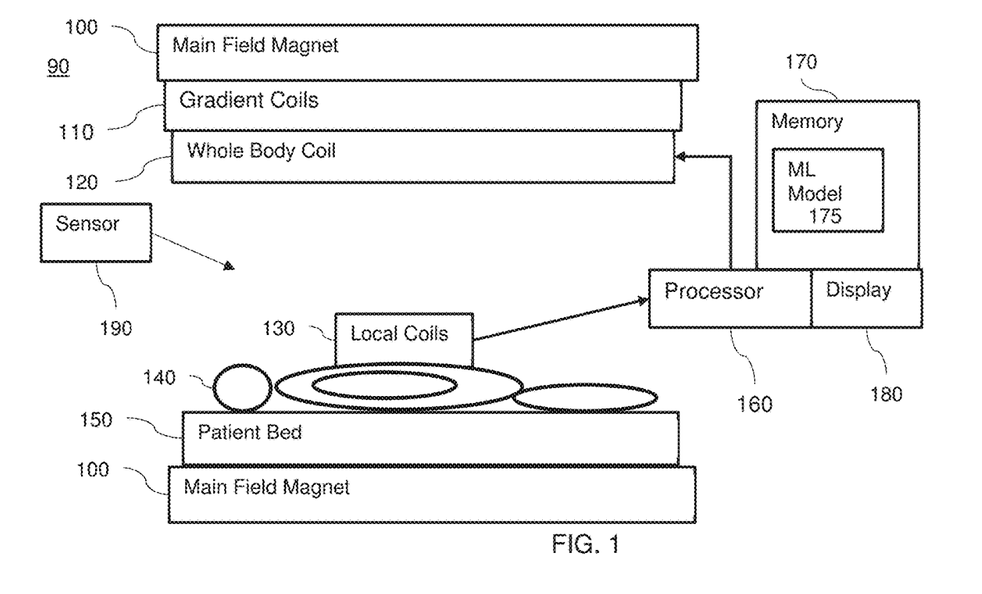
FIG. 1 is a block diagram of an embodiment of an MR system for autonomous medical imaging.

FIG. 1 shows one embodiment of a system for MR scanning by an MR scanner. The MR scanner 90 scans a given patient 140. The MR scanner 90 performs the acts of FIG. 2 or another method. The MR scanner 90 operates, at least in part, autonomously, including joint patient positioning and localization, adaptive configuration during scanning of a patient, and/or quality check analysis and adaptation. The MR scanner 90 may have reduced requirements, such as non-homogenous fields and/or non-linear gradients. The MR scanner 90 may be capable of image reconstruction but may use more rapid or different scanning for direct determination of an analytic from scan data.

The MR scanner 90 includes a main field magnet 100, gradient coils 110, whole body coil 120, local coils 130, and a patient support (e.g., bed) 150. The system includes the MR scanner 90, processor 160, memory 170, and display 180. One or more sensors 190 separate from the coils 110, 120, 130 may be provided. Additional, different, or fewer components may be provided for the MR scanner 90 and/or system. For example, the local coils 130 or the whole-body coil 120 are not used. In another example, the processor 160, memory 170, and display 180 are provided without the coils 100-120 and patient support 150, such as a workstation operating on scan data stored in the memory 170. In yet another example, the processor 160, memory 170, and/or display 180 are part of the MR scanner 90.

The MR scanner 90 is configured by settings of controls to scan a region of the patient 140. The scan provides scan data in a scan domain. The MR scanner 90 scans the patient 140 to provide raw measurements (measurements in a possibly non-linear frequency domain). Where hardware imperfections make the spatial encoding non-Fourier, the measured responses are referred to as raw data or scan data rather than k-space data. Where spatial encoding is Fourier, the scan or raw data may be k-space data. For the scan, the main field magnet 100 creates a static base magnetic field, B0, in the body of patient 140 positioned on the patient support 150. The gradient coils 110 produce position dependent magnetic field gradients superimposed on the static magnetic field. The gradient coils 110 produce position dependent and shimmed magnetic field gradients in three orthogonal directions and generate magnetic field pulse sequences. The whole-body coil 120 and/or the local coils 130 receive radio frequency (RF) transmit pulses, producing magnetic field pulses (B1) that rotate the spins of the protons in the imaged region of the patient 140.

In response to applied RF pulse signals, the whole-body coil 120 and/or local coils 130 receive MR signals, i.e., signals from the excited protons within the body as they return to an equilibrium position established by the static and gradient magnetic fields. The MR signals are detected and processed by a detector, providing an MR dataset of raw data. A raw storage array of the memory 170 stores corresponding individual measurements forming the MR dataset.

The MR scanner 90 is configured by the processor 160 to scan. Any of various scanner controls may be set, such as k-space coordinates, TR, TE, flip angle, pulse envelopes, carrier frequencies, timings, durations, and/or raw transmit pulses. A protocol, with or without user input or alteration, may establish the settings, at least initially, used for a particular scan. Any level of generality may be provided for the settings, such as an abstraction of the actual variables used for specific hardware. The memory 170 stores the configuration (e.g., a predetermined pulse sequence of an imaging protocol and a magnetic field gradient and strength data as well as data indicating timing, orientation, and spatial volume of gradient magnetic fields to be applied in scanning) and the resulting raw data or measurements.

The MR scanner 90 may be an image caliber MR scanner 90, such as having a homogenous B0 field provided by 0.5 T or higher field strength. An imaging caliber B0 field has, for example, <0.5 ppm VRMS over the volume of interest. The image caliber MR scanner 90 provides imaging caliber linear gradients, which have, for example, <2% geometric distortion.

In other embodiments, the MR scanner 90 has less restrictive design constraints, such as being designed and built for analytics without reconstruction and/or use for imaging. For example, a non-uniform main magnetic field (e.g., 10% variation in scan region of patient), non-homogeneous B0 field or transmit pulses (e.g., >0.5 ppm), and/or non-linear gradients (e.g., >2% geometric distortion) are provided. As another example, the main magnet 100 is 0.1 T or less. Where this less uniform magnetic field is needed, the bore in which the patient lies during scanning may be open. An open bore scanner allows sufficient space that a field of view of the sensor 190 may sense (e.g., take a picture or see) the patient within the bore. The field of view of the sensor 190 extends to the patient while the patient is within the open bore of the open bore MR scanner 90. For example, the open bore may be a chair or bed as the patient support 150 without a surrounding housing or may be a housing that is open at more than the two ends along a longitudinal direction of the patient 140, such as having open sides and open ends (i.e., housing above and below the patient but not to the top, bottom, or sides). As another example, the bore may be cylindrical, but over 4, 5, or 6 feet in diameter.

For a less restrictive design, the MR scanner 90 may be in a room without a faraday cage. Radio frequency shielding is not provided outside of or surrounding the MR scanner 90. In other embodiments, the MR scanner 90 is in a room formed as a faraday cage.

The patient support 150 is a flat or contoured slab (e.g., bed) on which the patient 140 lies or is supported. In an open bore, the patient support 150 may be formed as a recliner or chair given a larger bore.

The patient support 150 is movable relative to the MR scanner 90 (i.e., the main field magnet 100, gradient coils 110, and whole-body coil 120). A motor with gearing, pulleys, and/or other transmission moves the patient support into and out of the bore, such as longitudinally along the bore or patient support 150. Other motion may be provided, such as raising and lowering the patient support 150, moving the patient support 150 laterally (orthogonal to a side of the patient 140 lying on their back), and/or rotating along one, two, or three dimensions. One or more sensors may measure the location of the patient support 150 relative to the MR scanner 90.

The patient support 150 with the patient 140 is moved into the more or most homogeneous part of the magnetic field created by the main field magnet. Using the gradient coils 110, the MR scanner 90 may localize a region of interest or scan region at different locations in a field of view (FoV) of the MR scanner 90. The patient support 150 moves the patient 140 so that the region of interest is within the field of view of the MR scanner 90 to allow localization. For example, the prostate is to be scanned. The patient support 150 moves the lower abdomen of the patient 140 to be centered in the bore and/or within the bore. The MR scanner 90 then scans the prostate region and not other scannable regions with the patient 140 in the position established by the patient support 150. In alternative embodiments, the open bore allows the patient to move themselves within the bore or MR scanner 90 FoV.

The positioning by the patient support 150 and then the localization by the MR scanner 90 (i.e., identification and steering to scan the region of interest) may be handled sequentially. This may be the case where the bore blocks the sensor 190 from sensing the patient near the region of interest. Instead, a pilot or pre-MR scan is performed to locate the region of interest after the patient 140 is positioned by the patient support 150. In a less restrictive design with a larger or open bore, the sensor 190 may be used to find the region of interest for steering or localizing the MR scan, with or without also using pre-MR scanning. This allows both patient positioning and localization as a single unified step. The positioning and localization are handled jointly rather than sequentially. This allows control of mechanical actuators and external sensors to steer the MR fields. This is a direct consequence of open-bore low-field hardware concepts in which patient position can still be changed once in the FoV of the MR device, external sensors 190 still have access to the patient 140 in scanning position, and/or the MR scanner 90 might have a smaller FoV and require mechanical steps (i.e., patient support positioning) to reach a given ROI.

The sensor 190 is one or more sensors. The sensor 190 is positioned outside of the bore or MR scanner 90 FoV but may be within the bore. The sensor 190 mounts to the housing of the MR scanner 90, a robotic arm, wall, ceiling, or sensor tree. The sensor 190 is positioned so that the sensor FoV captures all or part of the patient 140 while the patient 140 is within the bore. For example, the sensor FoV reaches an exterior part of the patient 140 by the region of interest while the patient 140 is positioned by the patient support 150 where the MR scanner 90 may be localized to scan the region of interest.

The sensor 190 is an active or passive sensor. For example, the sensor 190 is a camera for acquiring optical images or a depth camera for acquiring optical images with depth. Infrared cameras or cameras for visual frequencies may be used. Other types of passive sensors may be provided, such as laser rangefinders, radio frequency sensors, or a weight mat sensing weight at different locations on the patient support 150. In an alternative, or additional, example, the sensor 190 is an active sensor, such as an ultrasound scanner that transmits acoustic energy in a steerable way and receives echoes or a camera on a robotic arm that actively moves the camera.

The processor 160 configures the MR scanner 90 and/or determines a value for one or more analytics from scan data. The processor 160 is a general processor, digital signal processor, graphics processing unit, application specific integrated circuit, field programmable gate array, artificial intelligence processor, tensor processor, digital circuit, analog circuit, combinations thereof, or another now known or later developed device for operating on raw data and/or applying artificial intelligence. The processor 160 is a single device, a plurality of devices, or a network. For more than one device, parallel or sequential division of processing may be used. Different devices making up the image processor may perform different functions, such as configuring the MR scanner 90 to scan by one device and determining an analytic based on raw data by another device. In one embodiment, the processor 160 is a control processor or other processor of the MR scanner 90. Other processors of the MR scanner 90 or external to the MR scanner 90 may be used.

The processor 160 is configured by software, firmware, and/or hardware to perform its tasks. The processor 160 operates pursuant to instructions stored on a non-transitory medium (e.g., memory 170) to perform various acts described herein.

The processor 160 is configured to jointly (1) position the patient 140 by movement of the patient support 150 and/or the MR scanner 90 and (2) localize the scan of the region by the MR scanner 90. Using the sensor 190 and/or MR scanning, the processor 160 solves for a patient support position and a localization of a scan region (e.g., region of interest) within the MR scanner FoV. The solution is joint, such as solving for both position and localization together. The solution may be iterative, such as moving the patient support 150 and setting the localization in a first solution, and then refining the solution.

In one embodiment, the processor 160 applies a machine-learned model 175 configured to jointly position and localize as a single solution for both the position and the localization. The machine-learned model may be a neural network that accepts sensor outputs as an input (e.g., from the sensor 190, any patient support position sensors, and/or MR scan data) and outputs a position at which the patient support 150 is to be placed and a location of the region of interest relative to the MR scanner FoV for localization. The machine-learned model is trained to control or act on the patient support 150 and MR scanner 90 to implement the solution without user input or control. For example, the machine-learned model is a machine-learned detector configured by training to detect the current position and localization from the output of the sensor 190 and scan data, and is a machine-learned actor configured to move the patient support 150 and/or change the localization where the detected position and/or localization is incorrect (not optimum or not workable, e.g., localization outside the MR scanner FoV).

In an alternative, or additional, embodiment, the processor 160 is configured to analyze the scan data once the patient is positioned and the scan localized. The analysis by a machine-learned model 175. The machine-learned model 175 is different than or is the same as the model used to position and localize. The machine-learned model 175 is configured by training to output a diagnosis in response to input of the scan data.

A diagnostic question, such as cancer or stage of cancer, is answered by the machine-learned model 175 in response to input of the scan data. For example, the processor 160 is configured to determine an analytic for the patient. The analytics may be a global analytic, such as a representing a characteristic of the patient in general rather than by location-by-location as in imaging. For example, the global analytic is a clinical finding, such as (1) no or possible cancer or (2) no need or need for further scanning or imaging. The processor 160 is configured to determine a value for the analytic by application of the machine-learned model 175 to the raw data without reconstruction from the raw data. The image reconstruction step is skipped or not provided. AI analytics are performed directly from the raw data to clinical findings as the diagnoses. The processor 160 uses the machine-learned model 175 to determine the analytic without reconstruction.

In another example, the processor 160 is configured to alter the settings based on the analysis. In addition to detecting the diagnosis, the processor 160 also configures the MR scanner 90. The initial configuration may be based on the diagnostic question or why the patient is being scanned. A default configuration is used. Once scanning starts, the processor 160 may alter the configuration. Based on the scan data acquired, the configuration is changed so that more relevant or determinative data is acquired. In one embodiment, the machine-learned model 175 includes a machine-learned actor that determines the configuration. The analysis of the scan data may be used by the actor, such as identifying desired data not yet sufficiently available. For example, back-propagation of the machine-learned model 175 used to answer the diagnostic question is used to identify the information (scan data) leading to greater uncertainty in the answer. The actor then configures the MR scanner 90 to reacquire that information or to acquire missing information.

The processor-driven alteration provides for reconfiguration during the scanning of the patient in a given or single examination. Rather than following a protocol designed to reconstruct a particular type of image, the combination of use of scanning for diagnosis and analysis of scan data allows for changing the scanning to more rapidly and/or thoroughly acquire the scan data to answer the diagnostic question more confidently.

In yet another additional, or alternative embodiment, the processor 160 is configured to monitor artifacts of the scan data and alter the scanning (e.g., settings or data to maintain) based on artifact level. For example, the machine-learned model 175 includes a machine-learned detector to detect artifacts in general or a specific type of artifact and includes a machine-learned actor to alter the scan configuration or workflow to address any detected artifacts.

The machine-learned model 175 is one or more models. Hierarchal, sequential, or other machine-learned model arrangements may be used. The machine-learned model 175 is formed from one or more networks and/or another machine-learned architecture (e.g., support vector machine). For example, and used herein, the machine-learned network is a deep-learned neural network. In another example, the machine-learned network is a neural network of a sequence of transformer and/or attention layers. In one embodiment, the machine-learned model 175 includes models for detection. Different events (e.g., position and localization, diagnostic value, and/or artifact) are detected by different machine-learned models or a common multi-task model trained to detect the different events. Different actions (e.g., move patient support and/or configure MR scanner 90 for localization, artifact reduction, and/or information gain to acquire information to answer the diagnostic question) are performed by a common machine-learned model (e.g., a reinforcement deep learned network or machine-trained actor) or different machine-learned models for the different actions.

The machine learned model 175 is trained by training data with or without ground truth. A loss based on output of the model being trained compared to an objective function or ground truth is used in an optimization to train the model. Any optimization may be used, such as Adam. Any loss may be used, such as cross entropy, L1 loss, or L2 loss. Pre-training, cross-training, and/or continuous training may be used. The training data is gathered from a database of examples performed under expert control. Ground truth may be curated or created by expert review. Instead, or in addition, the training data may be created by modeling or synthetically created using a model of MR scanning.

The memory 170 is a cache, buffer, RAM, removable media, hard drive, or another computer readable storage medium. Computer readable storage media include various types of volatile and nonvolatile storage media.

The memory 170 stores raw data, the settings for the controls, information derived from the settings, the machine-learned model 175, positions, localization, levels of artifact, and/or values for analytics. The memory 170 may alternatively or additionally store instructions for the processor 160. The functions, acts or tasks illustrated in the figures or described herein are executed by the processor 160 in response to one or more sets of instructions stored in or on the non-transitory computer readable storage media of the memory 170. The functions, acts or tasks are independent of the particular type of instructions set, storage media, processor or processing strategy and may be performed by software, hardware, integrated circuits, firmware, micro code and the like, operating alone or in combination.

In one embodiment, the instructions are stored on a removable media device for reading by local or remote systems. In other embodiments, the instructions are stored in a remote location for transfer through a computer network. In yet other embodiments, the instructions are stored within a given computer, CPU, GPU or system. Because some of the constituent system components and method steps depicted in the accompanying figures may be implemented in software, the actual connections between the system components (or the process steps) may differ depending upon the manner in which the present embodiments are programmed.

The display 180 is a CRT, LCD, plasma, projector, printer, or other display device. The display 180 is configured by loading an image to a display plane or buffer. The display 180 is configured to display the analytic, such as a value for each of one or more global analytics (e.g., clinical findings). The display may be of the value with or without a reconstructed image of the patient 140. For example, the display is part of a report, text result, or electronic health record for the patient. The display by the display 180 outputs the value for the analytic to assist the medical professional with decision making. For example, the value is that there is possible cancer of the prostate detected and/or that further scanning or imaging should be performed. Where the MR scanner 90 is a low-cost scanner with no or poor imaging capability, the scan may be used as a first test with cheaper equipment to determine whether more costly MR or other type of medical imaging should be performed.

Figure 2:
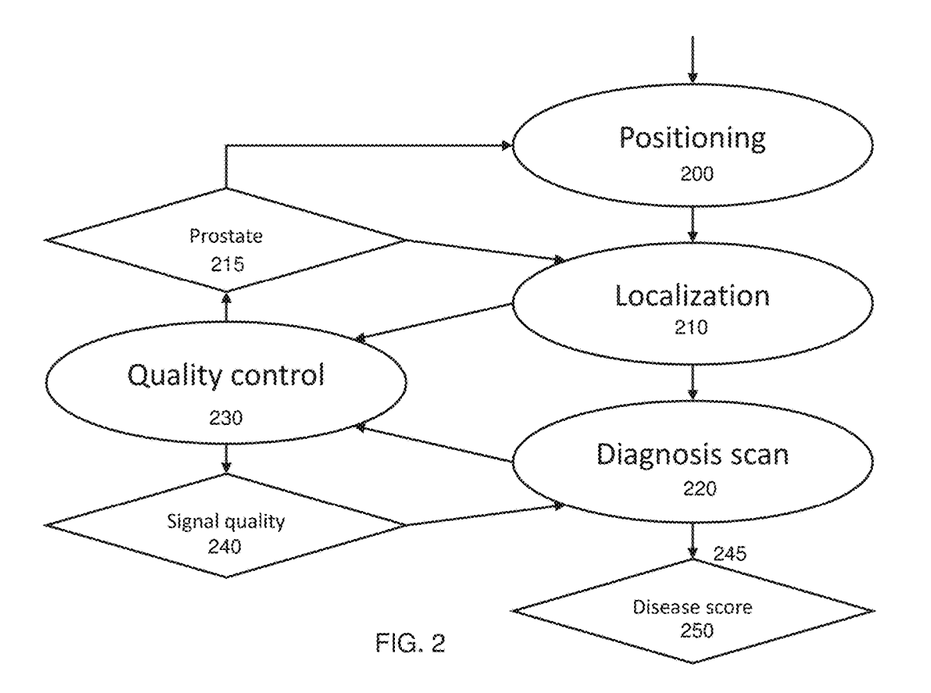
FIG. 2 is a flow chart diagram of one embodiment of a method for autonomous MR scanning.

FIG. 2 is a flow chart diagram of one embodiment of a method for autonomous MR scanning. The autonomous scanning is provided for a non-imaging or poor imaging MR scanner 90, allowing for a low cost, low technical expertise system to assist in diagnosis and/or deciding whether to perform a high-cost imaging scan. The method of data analytics provides for automation of positioning, localizing, MR scanning, analyzing, and generating output. These acts are performed without human control. Some human control may be provided to start the acts (e.g., automated push-button scanning) and/or initial protocol selection. In other embodiments, human control is provided for one or more acts.

The positioning 200, localization 210, quality control 230, and analysis for the diagnosis scan 220 may be autonomous using a machine-learned model or models. The method is performed by the system of FIG. 1 or another system. The MR scanner 90 scans the patient. A processor detects and/or acts based on information from sensors, MR scanning, and/or health records (e.g., scan order and/or clinical data for the patient). A display displays one or more clinical findings with or without a reconstructed image of the patient. Other components may be used, such as a remote server or a workstation performing the generation and/or display.

During application of the machine-learned model to one or more different patients and corresponding different scan data, the same learned weights or values of the machine-learned model are used. The model and values for the learnable parameters are not changed from one patient to the next, at least over a given time (e.g., weeks, months, or years) or given number of uses (e.g., tens or hundreds). These fixed values and corresponding fixed model are applied sequentially and/or by different processors to scan data for different patients. The model may be updated, such as retrained, or replaced but does not learn new values as part of application for a given patient. In other embodiments, continuous learning is used.

The method is performed in the order shown (top to bottom or numerical) or other orders. For example, acts 200 and 210 are performed together for solution (i.e., joint solution to patient support position and MR scanner localization), which solution may be implemented sequentially (move patient support, then configure scanner). Additional, different, or fewer acts may be provided. For example, a preset, default, or user input settings are used to configure the scanning prior to act 220. As another example, the value (disease score 250) is stored in a memory (e.g., computerized patient medical record), transmitted over a computer network, and/or displayed on the display.

In act 200, the processor positions the patient relative to the MR scanner. The patient support, with the patient on the patient support, is moved to position part of the patient within the FoV of the MR scanner. In act 210, the processor localizes the MR scanning. The MR scanning is steered or controlled to scan less than all of the scanner FoV, such as to scan a region of interest. The MR scanning is localized by setting the region relative to the MR scanner to scan.

Figure 3:
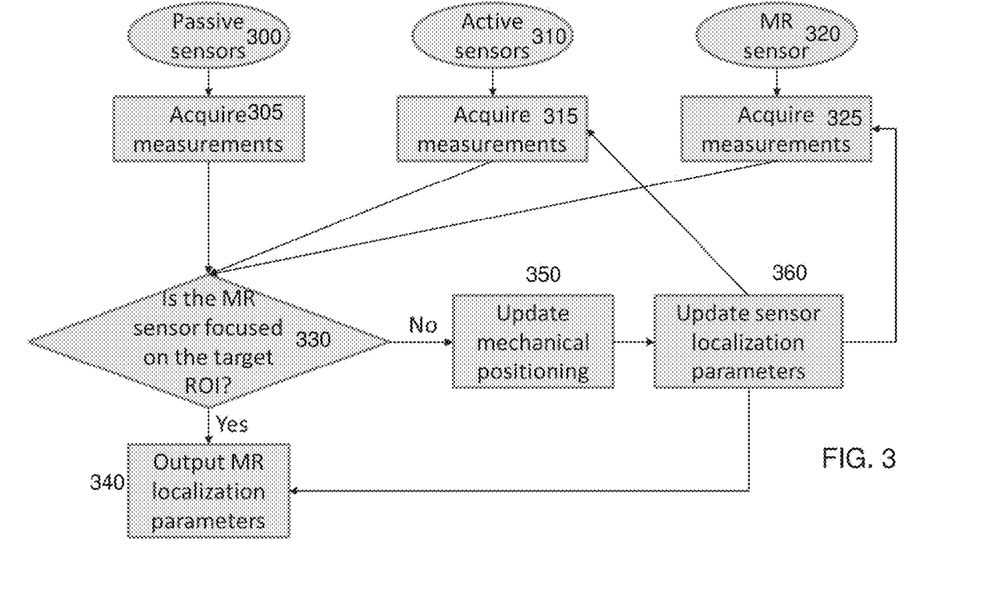
FIG. 3 is a flow chart diagram of one embodiment of a method for joint positioning and localization.

The positioning of act 200 and localization of act 210 refer to acts taken to ensure that the diagnostic scan covers the region of clinical interest (e.g., prostate). FIG. 3 shows an example embodiment. The patient is placed within a region (FoV) covered by the MR device itself (MR sensor 320) and/or other sensors such as video cameras, laser rangefinders, or RF sensors (passive sensors 300 and/or active sensors 310). The sensors 300, 310, 320 acquire measurements 305, 315, 325. The measurements 305, 315, 325 are provided to the processor to determine where the MR scanner 320 is focused on the target region of interest in act 330.

Depending on the MR scanner, positioning 350 can be achieved by using mechanical actuators such as electric motors or by providing feedback to the patient or technologist to help them reach a correct position. Localization updates the parameters of the MR device in act 360 (e.g., gradient strength, pulse carrier frequency, multicoil RF transmit and receive focusing) to focus the scan on the region of clinical interest. The localization parameters are output to the MR scanner in act 340. Localization parameters can be spatial coordinates of the target ROI in the room coordinate system or direct electrical controls to apply to the MR device to reach the ROI. The localization parameters may be provided to the active sensors 310 to steer the active sensors to examine or sense near the localized region of interest.

In a high-field scanner, homogeneous fields and linear gradients mean that the scanner is able to select cubes in the volume using a combination of slice selective excitations, frequency and phase readout encodings. In a low-field scanner, inhomogeneous fields and/or non-linear gradients may limit the FoV and corresponding number of cubes. The more open bore may allow for use of further patient support positioning in conjunction with localization to place the region of interest for scanning given the limits on the scanner FoV.

In one embodiment, the positioning of act 200 and localization of act 210 are implemented by a machine-learned model. The processor applies the measurements 305, 315, and/or 325 to the machine-learned model to jointly solve for the mechanical positioning 350 and the localization 360/340. The machine-learned model includes a machine-learned detector to determine where the region of interest is located relative to the MR scanner and/or whether the MR scanner is correctly focused on the target region of interest. The machine-learned model includes a machine-learned actor that changes the configurations of the device's mechanical degrees of freedom (e.g., positioning 350) as well as its sensors, including the MR sensor itself (e.g., update of localization 360). The machine-learned actor solves for all the change in location, such as patient positioning and MR scanner localization, in response to input.

In the example of FIG. 2, the positioning act 200 and localization act 210 are performed to position the prostate 215 of the patient for MR scanning. Other organs or regions may be the target.

In act 220, the MR scanner scans the patient using a configuration of the MR scanner. The scan is guided by a protocol, which establishes values for settings or control of the scanning. The scanning results in measurements. A pulse sequence (i.e., plurality of pulses from one or more coils) is created based on the configuration of the MR scanner (e.g., the imaging protocol selected). The pulse sequence is transmitted from coils into the patient. The resulting responses are measured by receiving radio frequency signals at the same or different coils. The scanning results in raw measurements as the scan data.

The protocol is for a medical test. The protocol is designed to provide scan data that may be used to reach a clinical finding. The scan data may be used to diagnose or answer a diagnostic question, such as whether more detailed scanning is needed, whether cancer exists in the organ, or a stage of cancer. The patient is referred to MR scanning for the clinical finding. For a given MR examination, the patient is positioned, the scan localized, and then the patient is scanned to find the clinical finding. The MR scanning continues over a period of seconds or minutes to acquire the scan data to answer the diagnostic questions.

The MR scanning may use an image caliber MR scanner. In other embodiments, an MR scanner with a non-uniform main magnetic field, non-homogeneous pulses, and/or non-linear gradients is used to scan.

The configuration established by the protocol may be updated during the scanning for the given examination. To reach the answer (e.g., clinical finding) with sufficient confidence, the configuration of the MR scanner is altered or updated during the examination.

Figure 4:
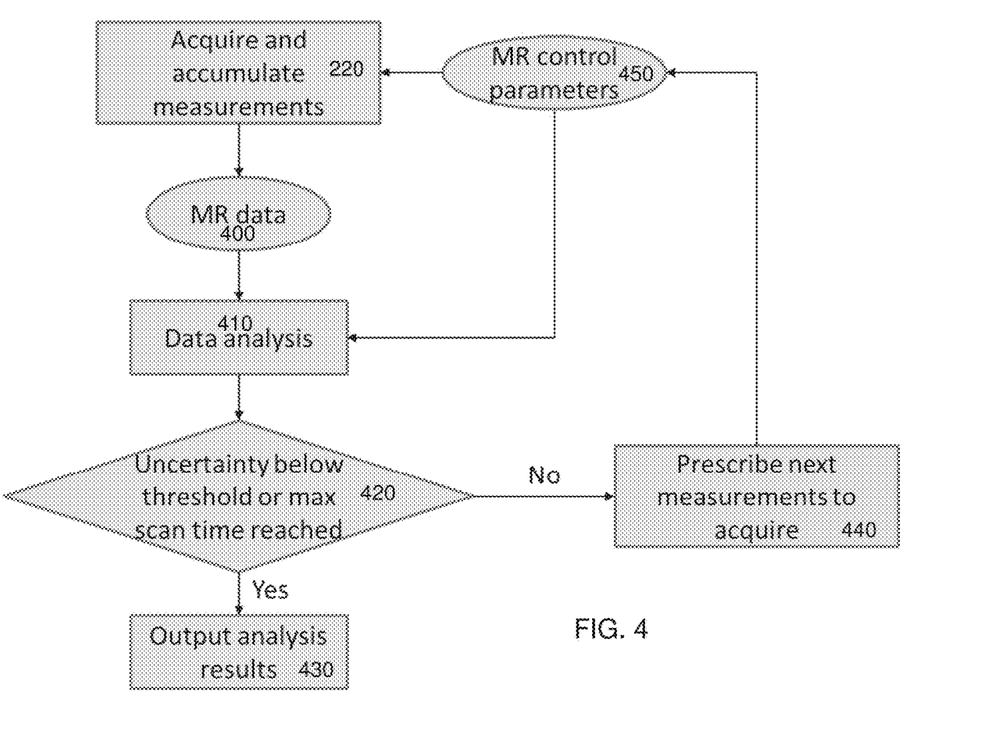
FIG. 4 is a flow chart diagram of one embodiment of a method for analysis to alter configuration during an MR examination.

FIG. 4 shows an example. MR control parameters 450 are initially established by the selected protocol (e.g., prostate examination). The scan data (MR measurements) 400 are acquired by scanning in act 220. In act 410, the processor (e.g., computer, workstation, server, or scanner processor) analyzes the scan data 400. The analysis may include analysis of the MR control parameters 450. The scan data 400 and control parameters 450 are analyzed to determine whether the configuration (control parameters 450) should be altered in act 420 and/or how to alter in act 440. The alteration is to acquire different measurements, so the parameters 450 are altered to acquire the desired measurements. During the MR examination, the MR scanning 220 is changed so that scan data optimized for the diagnosis is acquired.

In one embodiment, the processor uses a machine-learned model in the data analysis act 410. The scan data 400 and MR scan parameters 450 are input to the machine-learned model. The scan parameters 450 may be a type of scanner and/or settings of controls for the scanner (e.g., settings for a selected protocol). The scan parameters 450 may be the (1) specific scanner controls, such as k-space coordinates, repetition time, time-to-echo, and/or flip angle, (2) the pulse envelopes, carrier frequencies, timings, and durations of the pulses used in the MR scanning of act 220, or (3) the raw transmit pulses themselves or a representation of the transmit pulses. Other formats for the scan parameters may be used.

The machine-learned model, in response to the input, determines a value for the diagnosis for the medical test and an uncertainty for the value. The answer to the diagnostic question and the confidence in that answer are output. A neural network, regressor, or other machine-trained model may be trained to output the clinical finding or analytic value as well as an uncertainty for that value.

The machine-learned model generates a value for each of one or more analytics of the patient. The analytic is a parameter representing the patient. The parameter is not imaging or representation pixel-by-pixel or voxel-by-voxel, but instead represents more generalized information, such as a clinical finding. The analytic or parameter is a global characterization. While characterizing an organ, anatomy, and/or lesion, the characterization is general to the region rather than being for specific parts of the region. For example, the analytic is whether the patient has an indication of cancer or not. As another example, the analytic is whether a tumor is benign or malignant. In yet another example, the analytic is a cancer stage. One of the stages may be no cancer. As another example, the analytic is whether further scanning is recommended or not. The further scanning may be in the sense of further testing, whether by image scanning or by laboratory screening. Probabilistic or non-binary values may be generated, such as likelihood of cancer or not or another clinical finding.

In act 420, the processor determines that sufficient (Yes) or insufficient (No) information has been gathered by the MR scanning of act 220 using the configuration of the parameters 450. During the diagnosis scan, the MR scanner continuously acquires and analyzes measurements until the analytic confidently answers the clinical question for which the scan was scheduled. The acquired data 400 are continuously analyzed during acquisition so that the system can decide whether it has gathered enough information to reach a decision. The machine-learned model computes a measure of the uncertainty of the analytic. If the analytic is a categorical variable (e.g., the presence or absence of disease), then the uncertainty can be measured as the entropy of the posterior distribution of all the possible values of the analytic. If the analytic has a numerical value (e.g., the volume of an organ or lesion), then the uncertainty can be measured using a measure of the dispersion of the posterior distribution of the analytic such as its standard deviation. The uncertainty output by the machine-learned model is compared to a threshold level of confidence. If uncertainty is below the threshold (e.g., confidence above the threshold), the scan data 400 provides sufficient information to output the results in act 430. The value of the analytic is output.

If the confidence is low for the value of the analytic, the system then prescribes which measurements to acquire next in act 440 to maximize information gain with respect to the previously acquired data 400. The processor controls the MR scanner with a different configuration based on a change from the previous configuration. The configuration and corresponding MR control parameters 450 are changed to acquire further measurements (MR data 400) to more confidently answer the diagnostic question. The configuration is changed to gain information useful for the machine-learned model in detecting the value of the analytic.

In one embodiment, the machine-learned model is used to proscribe the next measurements in act 440. Backpropagation of the machine-learned model for determining the value of the analytic identifies the information most contributing to the uncertainty. This identifies missing or incorrect MR scan data 400, identifying what measurements to perform next. The measurements that provide the missing scan data or replace the incorrect MR data are proscribed in act 440. Alternatively, or additionally, the same or a different machine-learned model outputs the control parameters 450 and/or measurements desired in response to input of (1) the identification of the missing information or (2) the scan data 400 and parameters 450.

For data analysis in act 410, one or more machine-learned models may be used. For example, one machine-learned model (e.g., machine-learned detector) outputs a medical answer together with its uncertainty in response to input of the MR data 400 and the control parameters 450. Another machine-learned model is a machine-learned actor to proscribe measurements, set control parameters, or otherwise configure subsequent scanning 220 of the given examination.

For the machine-learned actors, a reinforcement-learned model may be used. Since the system contains actor components which impact future data collection, the system is machine trained using deep reinforcement learning. A policy for decision making is learned. Training data can be synthesized by physical simulation from a patient population generated using a clinical MRI dataset. The reward function in the reinforcement learning is a measure of the amount of relevant information acquired by the MR scanner, such as information gain with respect to the labels (i.e., analytic or disease) or uncertainty reduction in a label predictor based on the acquired data 400.

The system can be subdivided into parts and components for pre-training. The positioning and localization are one part. Diagnosis analysis is another part. Quality control is another part. The different parts may be pre-trained separately. The detector components (i.e., machine-learned detectors such as position detection, diagnosis data analysis, and quality control anomaly detection) are pre-trained using supervised training.

Once the detectors are trained, reinforcement learning of the actors is an inherently self-supervised process based on predicting future rewards, therefore the actors can continually improve on deployed devices. While it may not be acceptable to allow continuous learning to update the device behavior online, learning can also be performed without affecting the model behavior using off-policy sampling, i.e. use a released actor to select the actions, use those actions to train a continual actor, then trigger a release process including network quality checks once the continual actor is deemed to have sufficiently diverged from the released actor.

The machine-learned actor learns to make decisions or control through the entire process of FIG. 2. Alternatively, separate machine-learned actors are provided for the different components.

The machine-learned model as the detector and/or the actor has any of various architectures. For example, the machine-learned model is a neural network, such as a fully connected neural network (FCN) or a convolutional neural network (CNN). Any architecture or layer structure for machine learning may be used. The architecture defines the structure, learnable parameters, and relationships between parameters. In one embodiment, a convolutional or another neural network is used. Any number of layers and nodes within layers may be used. A DenseNet, encoder, autoencoder, CNN, FCN and/or another network may be used. Some of the network may include dense blocks (i.e., multiple layers in sequence outputting to the next layer as well as the final layer in the dense block). Any know known or later developed neural network may be used. Any number of hidden layers may be provided between the input layer and output layer. The model, as defined by the architecture, is trained.

Optimal control and reinforcement learning systems are synchronous systems that wait for the actor to decide the next action. However, real-time control might not be achievable for an MR scanner due to computational constraints, especially during the diagnosis part when the total latency between successive measurements might only be in the order of milliseconds. To enable optimal control without slowing down the scanner, the actor is implemented in an asynchronous way in which the scanner maintains a data-independent scanning plan (configuration) and follows the plan until the actor requests a change of plan in act 440. In this framework, the output of the scanning is a scanning plan, i.e., an open-ended generator of all future MR controls rather than just the controls of the next measurement. In that case, the output of the scanning actor is the parameters of the scanning plan model. The MR scanning 220 using the current configuration continues until the reinforcement learned model generates the change.

Referring again to FIG. 2, the scanning act 220 may be responsive to an act 230 for quality control. The signal quality 240 is determined and used in the control of the scanning of act 440 and/or analysis of act 410 as part of the scanning of act 220. The processor checks the quality of the raw data 400 from the scanning 220. The quality of the scan data is checked by a machine-learned model according to one embodiment for the quality control of act 230. The processor may then alters the configuration of the MR scanner in act 440 based on the quality and/or the missing information. The quality check may control by removal of information, so this influences the missing information used to proscribe further measurements. The quality check may control by alteration of parameters to avoid artifact, so this influences the scan parameters 450 used in the altered configuration. The quality control regularly or constantly monitors the acquired data to check whether the MR scanner, the patient, and/or the environment are behaving as expected as well as prescribing recovery steps in case of abnormalities.

A machine-learned model is used to determine quality in one embodiment. The quality is determined in general (not specific to a given type of artifact) or is determined for each of one or more different types of artifacts. The machine-learned model is a machine-learned detector to detect the level of artifact. The machine-learned model may be a machine-learned actor to control the scanning to increase the quality without input from a human. The actor causes the reconfiguration to improve quality without the user triggering and/or selecting settings to be used to improve quality. The actor may be separate from the machine-learned actor to alter the configuration for information gain or may be a common actor for making decisions related to both purposes.

In one embodiment, the quality check of act 230 checks for one or more specific artifacts. The configuration is altered to reduce that type of artifact. Identified error sources such as motion and RF interferences are monitored individually.

Figure 5:
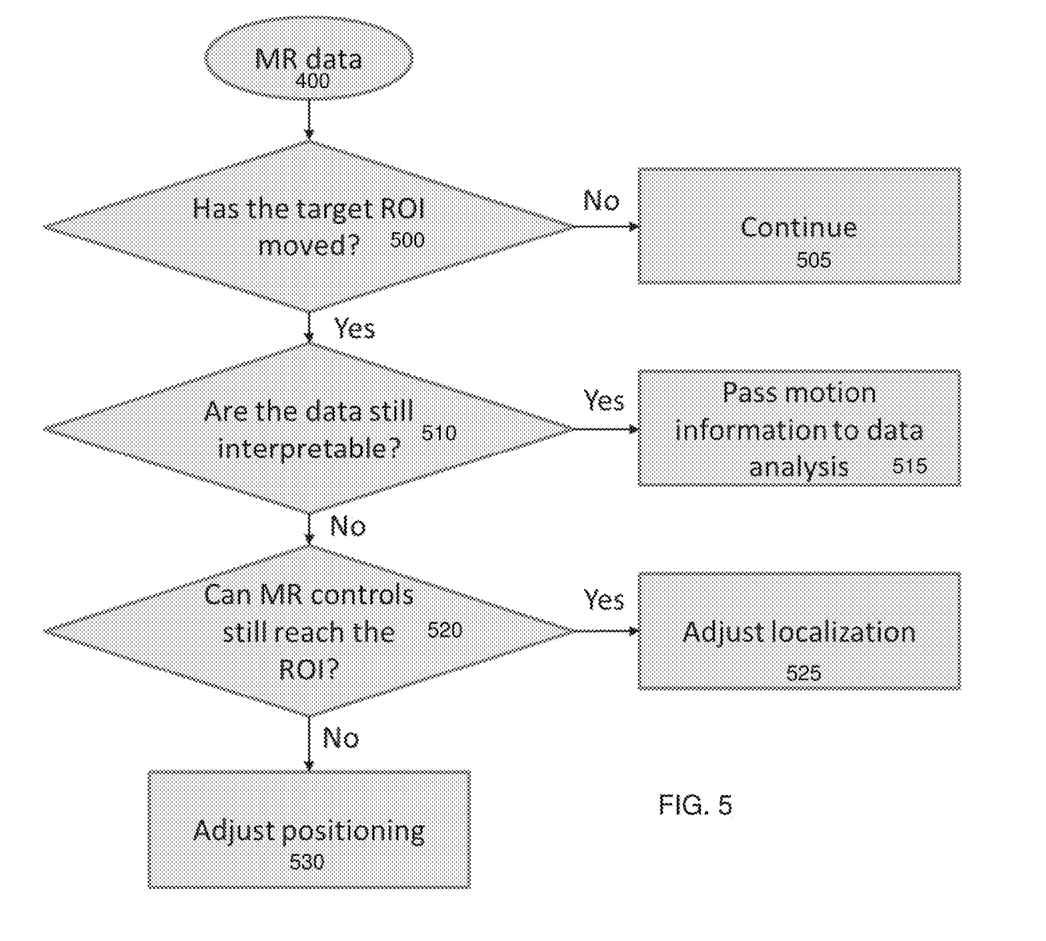
FIG. 5 is a flow chart diagram of one embodiment of a method for quality checking for motion artifacts as part of analysis to control scanning.

FIG. 5 shows an example of monitoring for and controlling to improve quality related to motion artifacts. The MR data 400 is analyzed to determine whether the patient has moved in act 500. Sensors may be used to monitor motion instead of or in addition to the MR data 400. If there is no movement or movement below a threshold, then the scanning continues in act 505. If there is movement over a threshold amount, the processor determines if the MR data 400 is still interpretable. If so, the motion information is passed to the data analysis of act 410. If not, the localization may be adjusted in act 525 where the region is still in the field of view of the MR scanner as determined at act 520. If not in the field of view, then the positioning of the patient support or patient is adjusted in act 530. In case of motion by the patient during the scanning 220, remediation steps can include adjustment to positioning and localization, adjustments to data analysis to take motion into account (type of imaging changed to diffusion and/or adjust data to account for motion), and providing feedback to the patient and/or operator.

Figure 6:
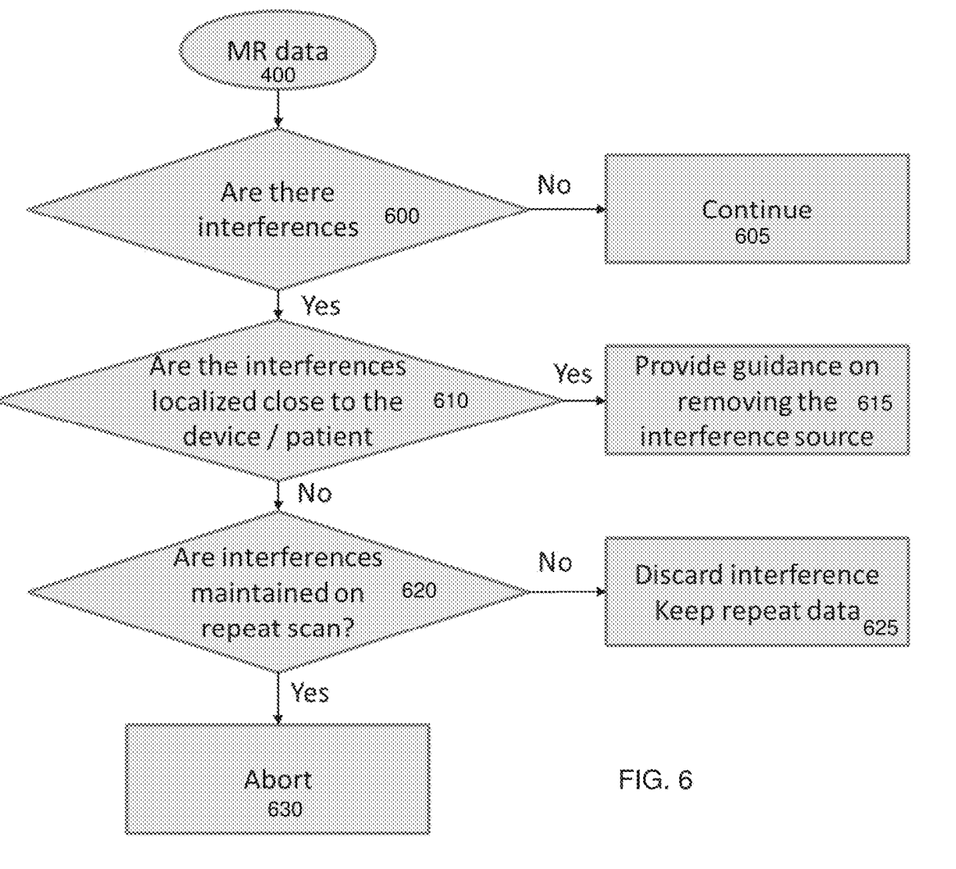
FIG. 6 is a flow chart diagram of one embodiment of a method for quality checking for radio frequency interference artifacts as part of analysis to control scanning.

FIG. 6 shows an example of monitoring for and controlling to improve quality related to radio frequency interference. The MR data 400 is checked for any interference in act 600. If none, then scanning continues in act 605. If there is some interference, then the interference is checked in act 610 for being localized close to the patient, such as the scan data reflecting that the patient has a phone or metallic object with them. If there is localized interference, guidance is provided in act 615 for removing the interfering source, such as outputting instructions to the patient. The scanning 220 is repeated and the check for interference repeated in act 620. If interference still exists, then the scan data 400 is discarded and the scanning is aborted in act 630. If there is no longer interference, then the MR data having shown interference is discard in act 625 and the MR data without interference or less interference is kept and used for data analysis in act 410. Remediation acts for radio frequency interferences may include feedback to the patient and/or operator if the interference source is identified as close to the scanner and under their control, and attempting to repeat measurements if the interference source is environmental but intermittent.

The quality control of act 230 may be implemented by processor application of a machine-learned model. The machine-learned model trained to output the value for the analytic may be a multi-task model also trained to output detection of an artifact. The machine-learned model trained to output the value of the analytic may use the quality indication as an input in assessing uncertainty. The machine-learned model trained to output a configuration or control scanning may receive artifact detection information to output the controls for scanning with less artifact and/or for rescanning.

In one embodiment, the check for detecting artifacts is for artifacts in general rather than specific to a given type of artifact. For example, a machine-learned model includes a machine-learned generator for generating a known good image or scan data. This machine-learned generator identifies deviation of the scan data from quality regardless of the type of artifact. This more generic abnormality detection is a one-class detection, which can also be performed to capture unidentified error sources. Unidentified artifacts have no associated remediation steps, however their detection can be considered by the data analysis in act 410 to assess uncertainty. Since one-class detection does not require supervision, this component can be continually trained after the device is deployed and the resulting machine-learned generator can be used as pre-training for the other trainable components. The anomalous data can also be mined and sent back to a central development hub for further root cause analysis.

After reconfiguration based on the data analysis for the analytic value and/or quality control, the MR scanner scans in act 220 to acquire the next measurements. Information for better certainty in the estimation of the diagnostic information by the machine-learned model is obtained by scanning directed to obtaining missing or incorrect (less artifact) information. This scanning is part of the same MR examination, so the patient does not leave the patient support and may perceive no delay or interruption to the MR scanning of this one or single appointment. The resulting scan or raw data may then be used for analysis and/or to generate the output value of the analytic. The method of FIG. 4 is repeated until the data analysis of act 410 indicates that the clinical finding has sufficient confidence or low uncertainty.

In act 245, the diagnostic output is generated. The output of the medical test of the MR examination is generated. This output is the value of the analytic or the answer (clinical finding) to the diagnostic question. An image of patient tissue may also be output or may not be output.

The output is generated from the scan data of the various iterations. The scan data is cumulative so that sufficient information with low enough artifacts is gathered for confident estimation by the machine-learned model of the diagnostic information. In alternative embodiments, the earlier scan data contributes to or is used to form the output by being analyzed and discarded, leading to reconfiguration and acquisition of better scan data used as input to generate the output.

A display (display screen or device) displays the output (e.g., value for the analytic). The value of the parameter representing the patient, such as the value of the clinical finding, is displayed. The display may be as part of a report for the patient, a pop-up, as a laboratory result, or as part of an electronic health record for the patient. The value is displayed as alphanumeric text, a graphic, or in a graph or chart. The value may be displayed without an image of the anatomy of the patient. In other embodiments, the value is displayed with an image of the anatomy of the patient, such as an image acquired with a non-MR modality (e.g., x-ray) or an image reconstructed from the MR scan.

The display presents the value for viewing by the user, radiologist, physician, clinician, and/or patient. The value assists in diagnosis.

Although the subject matter has been described in terms of exemplary embodiments, it is not limited thereto. Rather, the appended claims should be construed broadly, to include other variants and embodiments, which can be made by those skilled in the art.

What is claimed is:

1. A method of data analytics for magnetic resonance (MR) scanning, the method comprising:
    MR scanning a patient using a first configuration of an MR scanner based on a medical test during a MR examination and resulting in first raw data;
    analyzing, by a first machine-learned model, the first raw data, the analyzing resulting in a change of the first configuration;
    controlling the MR scanner with a second configuration based on the change from the first configuration;
    MR scanning the patient using the second configuration of the MR scanner for the medical test as part of the same MR examination and resulting in second raw data; and
    generating a diagnostic output of the medical test of the MR examination from the first and second raw data.

2. The method of claim 1 wherein MR scanning using the first and second configurations comprises MR scanning with a non-uniform main magnetic field, non-homogeneous first pulses, and/or non-linear gradients.

3. The method of claim 1 wherein analyzing comprises determining a value for a diagnosis for the medical test by the first machine-learned model and an uncertainty for the value, and wherein controlling comprises altering from the first configuration to the second configuration where the uncertainty is above a threshold.

4. The method of claim 3 wherein controlling further comprises proscribing next measurements based on backpropagation of the first machine-learned model and setting parameters of the second configuration for the next measurements based on missing information identified by the backpropagation.

5. The method of claim 1 wherein analyzing comprises determining that insufficient information has been gathered by the MR scanning using the first configuration and wherein controlling comprises determining the second configuration to gain the information.

6. The method of claim 1 wherein analyzing comprises inputting the first raw data and the first configuration to the first machine-learned model and outputting by the first machine-learned model the diagnostic output as an answer to a diagnostic question.

7. The method of claim 1 further comprising positioning a patient relative to the MR scanner and localizing the MR scanning by a second machine-learned model solving for both the positioning and the localizing.

8. The method of claim 1 further comprising checking quality of the first raw data by a second machine-learned model, wherein controlling comprises controlling to increase the quality without input from a human.

9. The method of claim 1 wherein controlling comprises controlling by a second machine-learned model, the second machine-learned model comprising a reinforcement learned model.

10. The method of claim 9 wherein MR scanning using the first configuration continues until the reinforcement learned model generates the change.

11. A magnetic resonance (MR) system comprising:
    a MR scanner configured by settings of controls to scan a region of a patient, the scan providing scan data;
    a patient support for the patient, the patient support moveable relative to the MR scanner;
    a sensor configured to sense the patient on the patient support;
    a processor configured to jointly (1) position the patient by movement of the patient support and/or the MR scanner and (2) localize the scan of the region by the MR scanner, wherein the processor comprises a machine-learned detector configured to detect the position and localization from input of an output of the sensor and the scan data and comprises a machine-learned actor configured to move the patient support and change the localization when the detected position and localization is incorrect.

12. The MR system of claim 11 wherein the processor comprises a machine-learned model configured to jointly position and localize as a single solution for both the position and the localization.

13. The MR system of claim 11 wherein the processor is further configured to analyze the scan data once the patient is positioned and the scan localized, the analysis by a machine-learned model configured to output a diagnosis in response to input of the scan data, and further configured to alter the settings based on the analysis.

14. The MR system of claim 13 wherein the processor is further configured to monitor artifacts of the scan data and alter the settings based on artifact level.

15. The MR system of claim 11 wherein the sensor comprises a camera and the MR scanner comprises an open bore MR scanner where a field of view of the camera extends to the patient while localized within an open bore of the open bore MR scanner.

16. A method for autonomous magnetic resonance (MR) scanning, the method comprising:
    positioning a patient in an MR scanner;
    localizing a region of the patient by the MR scanner for scanning the region;
    MR scanning the patient by the MR scanner, the MR scanning resulting in scan data;
    analyzing the scan data by checking a quality of the scan data by a machine-learned model; and
    generating a diagnostic answer from the scan data;
    wherein positioning, localizing, MR scanning, analyzing, and generating are performed without human control.

17. The method of claim 16 further comprising altering, by a processor, a configuration of the MR scanner based on the quality.

18. The method of claim 17 wherein checking comprises checking by the machine-learned model comprising a machine-learned generator of quality used to identify deviation from the quality regardless of a type of artifact.

19. The method of claim 17 wherein checking comprises checking for a type of artifact, and wherein altering comprises altering the configuration to reduce the type of artifact.

* * * * *